United States Patent [19]

Brunetti et al.

[11] Patent Number: 4,929,601
[45] Date of Patent: May 29, 1990

[54] TRIPEPTIDES USEFUL AS IMMUNOSTIMULANTS AS WELL AS IN THE PREVENTION OF METASTASES

[75] Inventors: Brunetto Brunetti, Milan; Marco Prada, Casalpusterlengo, both of Italy

[73] Assignee: Ellem Industria Farmaceutica, S.p.A., Milan, Italy

[21] Appl. No.: 227,356

[22] Filed: Aug. 2, 1988

[30] Foreign Application Priority Data

Aug. 4, 1987 [IT] Italy ................. 21575 A/87

[51] Int. Cl.$^5$ .................. A61K 37/02; C07K 5/08
[52] U.S. Cl. ........................ 514/18; 530/331
[58] Field of Search ................ 514/18; 530/331

[56] References Cited

U.S. PATENT DOCUMENTS

| 4,428,938 | 1/1984 | Kisfaludy et al. | 530/331 |
| 4,508,710 | 4/1985 | DeBarbieri et al. | 530/331 |
| 4,716,151 | 12/1987 | Jolles et al. | 530/331 |
| 4,743,590 | 5/1988 | DeBarbieri et al. | 530/331 |

OTHER PUBLICATIONS

Lam et al. Evidence that Arginyl–Glycyl . . . J. of Bio. Chem., Jan. 25, 1987, pp. 947–950.
Humphreys et al. Science vol. 233, A Synthetic Peptide from . . . Jul. 25, 1986, pp. 467–470.
Ruoslahti et al. Arg–Gly–Asp: . . . Cell, vol. 44, pp. 517–518, Feb. 28, 1986.

Primary Examiner—Lester L. Lee
Attorney, Agent, or Firm—Birch, Stewart, Kolasch & Birch

[57] ABSTRACT

The present invention is referred to tripeptides having the following general formula:

X-Gly-Y where X=L-Arg or D-Arg and Y=L-Asp or D-Asp.

These tripeptides, endowed with both immunostimulant and antimetastatic properties, are active not only after parenteral administration, but also after oral treatment.

The invention is also related to the procedure for the preparation of said compounds.

11 Claims, 2 Drawing Sheets

FIG.1: Profile HPLC di Arg-Gly-Asp
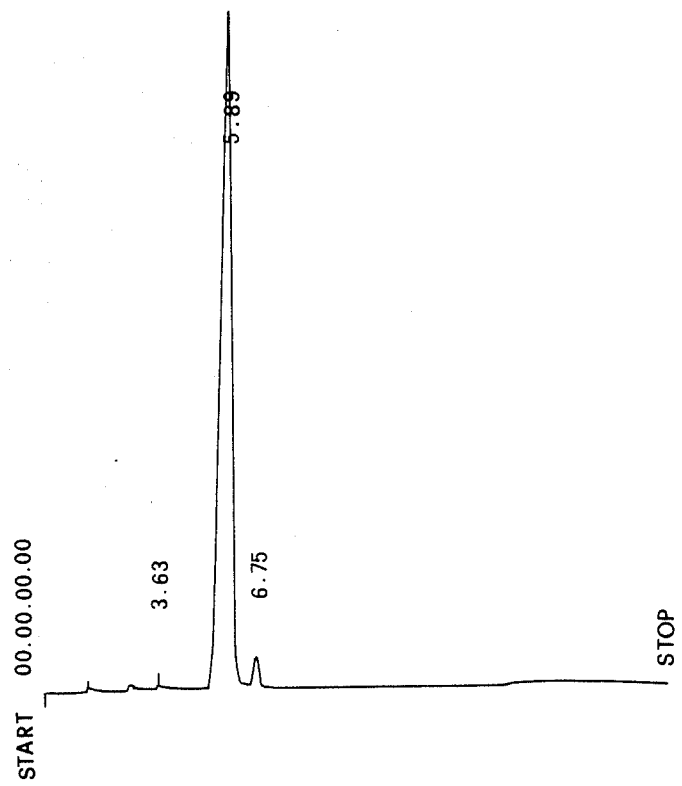

FIG. 2: Profile HPLC di Arg-Gly-D-Asp
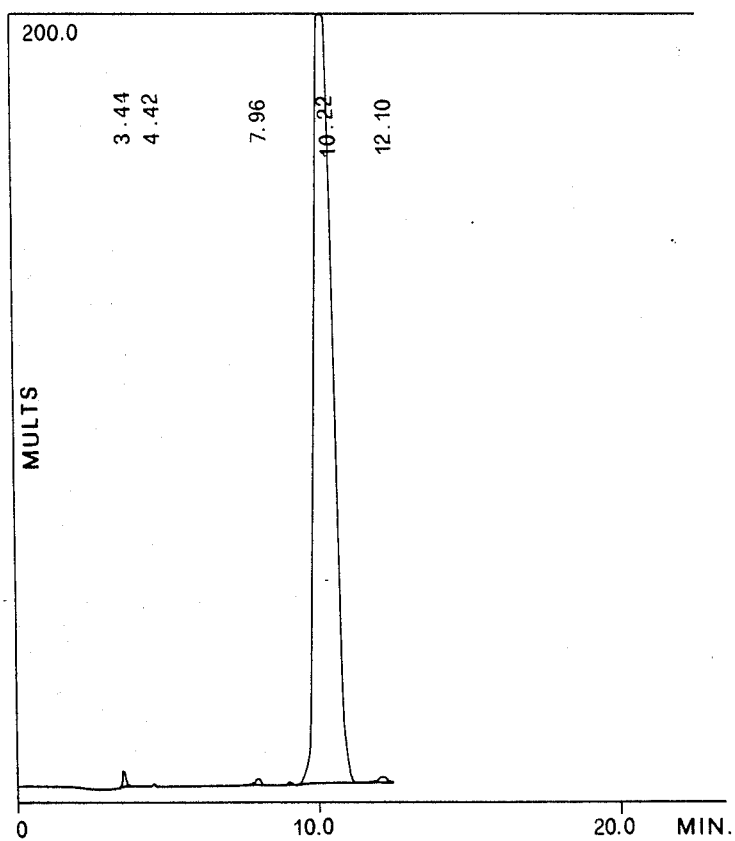

TRIPEPTIDES USEFUL AS IMMUNOSTIMULANTS AS WELL AS IN THE PREVENTION OF METASTASES

BACKGROUND OF THE INVENTION

It is known that the interaction between tumour cells and the extra-cellular matrix, caused or favoured by fibronectin, is inhibited by the intravenous administration of the synthetic pentapeptide Gly-Arg-Gly-Asp-Ser, whose sequence is the same as that of the cell-binding site of fibronectin (Humphries M. J. et al, SCience 233:467,1986).

Ruoslahti and Pierschbacher (Cell 44:517,1986) have proposed the hypothesis that the biological activity of this pentapeptide could be attributed to the tripeptide sequence Arg-Gly-Asp contained in it, without however testing the activity of the latter.

Lam et al (J. Biol. Chem. 262:947,1987) have instead proved that Arg-Gly-Asp is able to bind to some platelet surface glycoproteins, thus suggesting a possible biological action of this tripeptide as an inhibitor of platelet adhesion reactions.

Starting from the knowledge resulting from the above-mentioned state of the art, the applicant has synthesized some tripeptides belonging to the general formula X-Gly-Y, where X is L-Arg or D-Arg and Y is L-Asp or D-Asp, evaluating then their efficacy in experimental tests of antimetastatic activity.

The results have confirmed their efficacy as antimetastatic agents, but have also surprisingly shown their marked immunostimulating activity, not predictable on the basis of the present knowledge.

This immunostimulanting effect has been observed in vitro in experimental murine as well as human models and consists both in a maturation of immature T lymphocytes and in an enhancement of T cell function.

A similar immunostimulating behaviour has been described for the tripeptides Arg-Lys-Glu (U.S. patent application Ser. No. 035,045 of Apr. 6, 1987), Arg-Ala-Arg (U.S. patent application No. 035.044W of Apr. 6, 1987) and Arg-Lys-Asp (European patent application No. 67425 of Dec. 22, 1982).

Moreover, the tripeptides which are the object of the present invention have shown stability in simulated gastric juice: on the basis of what had been observed in the case of the peptides Arg-Lys-Glu and Arg-Ala-Arg, whose stability in simulated gastric ambient was coupled to activity after oral administration to animals, it is possible to attribute to the tripeptides which are the object of the present invention an immunostimulating activity after oral, besides parenteral, administration.

This represents a remarkable advantage in the therapeutical use, with particular reference to children and other patients who do not tolerate the parenteral administration, and also in view of a better patient compliance.

On the basis of what has been above mentioned, these products result to be very userful in the prevention of metastatization in neoplastic patients after surgical removal of the tumour, as well as in the contemporaneous stimulation of the immune system, depressed by both the radiochemotherapic treatments and the operation itself: both these factors are in fact notoriously immunodepressant.

Moreover, the availability of drugs which can be administered by oral route represents, for the therapy of these patients, another undoubted advantage.

SUMMARY OF THE INVENTION

The present invention describes the synthesis and the chemical as well as biological characteristics of a new class of tripeptides, defined by the general formula X-Gly-Y, where X is L-Arg or D-Arg and Y is L-Asp or D-Asp.

These products are characterized by the fact of being endowed with antimetastatic properties, observed in the test of murine melanoma experimental metastases, as well as immunostimulanting activity, shown in vitro in tests of murine spleen lymphocyte maturation (Thy 1.2 membrane marker induction) and in assays concerning the activation of human mature lymphocyte function (growth factor production, DNA and RNA synthesis after mitogenic stimulus, increase of mitoses).

Moreover, in vitro tests carried out in simulated gastric ambient have shown the stability of these peptides, so that it is possible to foresee their activity also after oral administration.

Thus, the products which are the object of the present invention can be used, thanks to their unique combination of antimetastatic and immunostimulating activities, as drugs in patients who undergo the surgical tumour removal, in order to prevent the metastasis formation, at the same time helping to improve the immune status.

DESCRIPTION OF THE DRAWINGS

FIGS. 1 and 2 represent, respectively, the HPLC profiles of the tripeptides Arg-Gly-Asp and Arg-Gly-D-Asp, obtained according to the methods described in the example 2.

DESCRIPTION OF THE INVENTION

The invention will be better understood through the following examples in which the following abbreviations are used:

Arg=L-arginine
Gly=glycine
Asp=L-aspartic acid
Asx=L-aspartic acid, D-aspartic acid or asparagine
D-Asp=D-aspartic acid
Boc=butyloxycarbonyl
N$^g$=Substitution on the guanoisine nitrogen of Arg.

EXAMPLE 1

Synthesis

Synthesis of L-Arginyl-glycyl-L-aspartic Acid 1. t-Butyloxycarbonyl-glycyl-L-aspartic acid dibenzyl ester t-Butyloxycarbonyl-glycine (7.1 g) was dissolved in ethyl acetate (50 ml), cooled to −10° to −15° C. with stirring and treated with N-methylmorpholine (5.6 ml) followed by isobutyl chloroformate (5.18 ml). The mixture was stirred at −15° C. for 10 minutes. Meanwhile, L-aspartic acid dibenzyl ester p-tosylate salt (2°.1 g) was dissolved in dimethyl formamide (80 ml), cooled to −10° C. and neutralized by adding N-methylmorpholine (5.6 ml). This solution was added to the above solution of the preformed mixed anhydride and the reaction mixture allowed to warm slowly to room temperature with stirring over 3 hours.

The reaction mixture was then diluted with ethyl acetate (300 ml) and the solution washed with brine (twice) followed by 4% aqueous sodium bicarbonate, water, 5% aqueous citric acid and finally with water to neutrality. The organic phase was dried (magnesium sulfate) and then evaporated to an oil. Yield: 20 g. The product was homogeneous by TLC (System: chloroform:methanol:acetic acid, 360:32:8; $R_f$=0.8).

2. Tribenzyloxycarbonyl-L-arginyl-glycyl-L-aspartic acid dibenzyl ester

The product from the previous step (20 g) was treated with 50% trifluoroacetic acid in methylene chloride (125 ml) for 25 minutes at room temperature and the solvents evaporated under reduced pressure.

The residue was re-evaporated from toluene and then dried in vacuo. The resulting trifluoroacetate salt of the dipeptide was dissolved in dimethyl formamide (75 ml), cooled to −10° C. and neutralized by treating with N-methylmorpholine (5.6 ml). Meanwhile, tribenzyloxicarbonyl-L-arginine (23.1 g) was converted to the mixed anhydride by dissolving in tetrahydrofuran (100 ml), cooling to −10° to −15° C. and treating with N-methylmorpholine (5.6 ml) followed by isobutyl chloroformate (5.18 ml) as described above. The precooled solution of the neutralized dipeptide was added to the solution of the mixed anhydride and the mixture stirred for 3 hours, warming slowly to room temperature. During the course of the reaction, the mixture solidified and dimethyl formamide (50 ml) was added to facilitate stirring. The tetrahydrofuran was evaporated under reduced pressure and the residue diluted with ethyl acetate (500 ml).

This solution was washed with saturated aqueous sodium chloride, during which a white solid precipitated. This solid was filtered off, washed with ethyl acetate and dried to give the protected tripeptide. Yield: 25 g. Thin layer chromatography (System: chloroform:methanol:acetic acid, 85:10:5) showed a slight contamination by unreacted tribenzyloxycarbonylarginine. The product (14 g) was therefore purified by dissolving in chloroform:methanol (98:2) and applying to a column of silica gel (600 g). The Column was eluted with progressively increasing amounts of methanol in chloroform to give the pure protected tripeptide. Yield: 10 g.

3. L-Arginyl-glycyl-L-aspartic acid

The protected tripeptide from the previous step (10 g) was hydrogenated at 50 psi in methanol-acetic acid-water (60:20:20, 300 ml) for 72 hours over palladium on carbon (5%, 3 g), when reaction was complete by TLC. The catalyst was filtered off, the methanol evaporated under reduced pressure and the residue lyophilized to give the tripeptide as a white powder. Yield: 3 g. The product was homogeneous by thin layer chromatography (Systems: A, isopropanol:ammonia,1:1; B, n-butanol-acetic acid:water:pyridine, 60:12:40:48).

Synthesis of L-Arginyl-glycyl-D-Aspartic acid

1. Preparation of Boc-β-Benzyl-D-Aspartic Acid-Resins

Chloromethylated polystyrene (1% crosslinked; 200–400 mesh) was placed in a round-bottom flask and swollen in dimethylformamide (approximately 8–10 ml per gram of resin), then treated with the Boc-β-benzyl-D-aspartic acid (1 mmole per gram of resin), followed by potassium fluoride (2 mmole per gram of resin). The flask was equipped with a mechanical stirrer and condenser and heated under vacuum until a small amount (5–10 ml) of the solvent had distilled. The vacuum source was removed and the mixture heated to 80°–100° C. for 16–18 hours. On cooling, the resin was filtered, washed with dimethylformamide, dimethylformamide:water (1:1), water, ethanol, dichloromethane and methanol, and then dried under vacuum. Substitution (as calculated by weight gain)=0.6 mmole per gram.

2. Synthesis protocol

A quantity of 17.6 grams of Boc-β-benzyl-D-aspartic acid-resin was placed in a glass reaction vessel equipped with a mechanical stirrer, a sintered glass base and a vacuum source for filtration. The resin was treated sequentially at ambient temperature (20°–25° C.) with the following solvents or reagent:

a. methylene chloride
 b. 50% trifluoroacetic acid:methylene chloride (v/v)
 c. 50% trifluoroacetic acid:methylene chloride for 25 minutes.
 d. methylene chloride (3 times)
 e. isopropanol
 f. 10% triethylamine:methylene chloride (v/v) (twice)
 g. methylene chloride
 h. methanol (twice)
 i. methylene chloride (twice)

A contact time of 3–5 minutes was allowed for each treatment.

Approximately 10–15 ml of solvent or reagent-solvent mixture per gram of resin was used in each step.

j. The resin was stirred with a solution of Boc-glycine (3 equivalents) in methylene chloride, and to this was added dicyclohexylcarbodiimide (3 equivalents) in methylene chloride. The reaction time for coupling was a minimum of 2–4 hours but could be overnight (16–18 hours). The peptide-resin was filtered and washed with methylene chloride, methanol and methylene chloride and checked for completeness of coupling by the ninhydrin reaction. If coupling was incomplete, the same amino acid was recoupled using half the amount of reagents.

The cycle was repeated for Boc-$N^g$-tosyl-L-arginine (in dimethylformamide). After removal of the N-terminal Boc-group, the resin peptide was washed thoroughly and dried under vacuum.

Yield of resin-peptide: 21.0 g.

The peptide was cleaved from the resin and deprotected concomitantly by treatment with anhydrous liquid hydrogen fluoride (approximately 10 ml per gram of resin-peptide) containing anisole (10% v/v) for 1 hour at 0° C. After evaporation of the hydrogen fluoride under reduced pressure, the crude peptide was extracted by washing the resin with dilute, aqueous acetic acid and the product isolated by lyophilization.

Yield of crude peptide: 3.9 g.

3. Purification of the crude peptide

The crude peptide could be purified by preparative, reversephase HPLC using C18-derivatized silica, using, for example, a Waters Prep 500 instrument. Using a 5×30 cm column, equilibrated with the appropriate aqueous buffer, such as 0.1% aqueous trifluoroacetic acid, the crude p-ptide (approximately 2 grams) was applied to the column and eluted with a gradient containing increasing amounts of acetonitrile. Fractions were monitored by analytical HPLC and those containing the product at the desired level of purity (>97%) were combined and lyophilized. Finally, the purified product was converted to its desired salt by treatment with the desired salt form of an ion exchange resin.

Yield of purified peptide as acetate salt: 2.5 g.

EXAMPLE 2

Chemical Characteristics

Arg-Gly-Asp

The data here shown are referred to a single batch of the tripeptide and should not be considered in a restricted manner.

Molecular weight: 346.4
Appearance: white powder
Amino acid analysis:

| Amino acid | Theory | Found |
| --- | --- | --- |
| Asx | 1.00 | 1.00 |
| Arg | 1.00 | 0.98 |
| Gly | 1.00 | 1.02 |

Peptide content: 78.5%
Peptide purity: 96%
Humidity: 6.56
TLC: Isopropanol:NH3 (1:1) purity 99%, Rf=0.75
HPLC: the analysis has been carried out according to the methods hereafter described and the profile is shown in FIG. 1:
Solvents:
  A=KH2P04 0.05M
  B=60% CH3CN+40% A
Gradient: from 0 to 10% B in 20 minutes
Column: Ultrasphere ODS (ALtex)
Sensitivity: 0.2 AUFS
Wavelength: 210 nm
Flow rate: 1.5 ml/minute
Minimum area: 10

Arg-Gly-D-Asp

The data here shown are referred to a single batch of the tripeptide and should not be considered in a restricted manner.

Molecular weight: 346.4
Appearance: white powder
Amino acid analysis:

| Amino acid | Theory | Found |
| --- | --- | --- |
| Asx | 1.00 | 0.94 |
| Arg | 1.00 | 1.05 |
| Gly | 1.00 | 1.02 |

Peptide content: 80.5%
Peptide purity: >98%
HPLC: the analysis has been carried out according to the methods hereafter described and the profile is shown in FIG. 2:
Solvents:
  A=NaH2P0425 m, 50 nM NaClO4, pH 3.0 with H3P04
  B=H20:MeCN 1:1
Gradient:
  from 0 to 30% B in 15 minutes, linear
  from 30 to 70% B in 10 minutes, linear
Column: Deltapack C18 (5 μm, 100 Å) 3.9×150 mm
Sensitivity: 0.2 AUFS
Wavelength: 220 nm
Flow rate: 0.7 ml/minute
Minimum area: 10

EXAMPLE 3

Biological Characteristics

Stability in simulated gastric ambient in vitro

The tripeptide Arg-Gly-Asp has resulted to be stable at 37° C. for 3 hours in simulated gastric ambient in vitro using the solution of simulated gastric juice USP XXI (HCl+pepsin).

Antimetastatic activity

The capacity of the tripeptide Arg-Gly-Asp of inhibiting the pulmonary colonization by B16-BL6 murine melanoma cells inoculated in female C57BL/6 mice having an average body weight of 20 g (10 animals per group) has been evaluated.

Arg-Gly-Asp has been administered at the dose of 3 mg/mouse by intravenous injection together with $2 \times 10^5$ melanoma cells.

Fourteen days later, the animals have been sacrificed, the lungs have been withdrawn and examined after formalin fixation for the presence of surface melanoma colonies. A group of control animals has only been treated with the tumour cell suspension.

While in the controls the mean number of metastases was above 500/mouse, this value was reduced in treated animals, where it was 173/mouse.

By administering $7 \times 10^4$ tumour cells, the mean number of metastases in the controls was 21.6, decreased to 6.8 in animals treated with 3 mg/mouse i.v. of Arg-Gly-Asp (−69%).

Induction of Thy 1.2 antigen in spleen cells of normal mice

The capacity of the tripeptide Arg-Gly-Asp to induce in vitro the differentiation of T cell precursors into lymphocytes expressing T cell markers has been tested by evidencing the induction of Thy 1.2 membrane antigen.

Cell Preparation

Spleen cells of normal mice have been used as source of "null" cells.

Mice were killed by cervical dislocation.

Spleens were aseptically removed and finely minced with forceps in Hank's balanced salt solution (HBSS) (Gibco Ltd, Paisley, Scotland). A suspension of single cells was obtained through filtration on a fine mesh wire sieve. Mononuclear cells (MNC) have been isolated through differential centrifugation on Lymphoprep (Nyegaard, Oslo, Norway) with continuous density gradient for 20 minutes at 450 g.

After 3 washes in HBSS, MNC were suspended at a concentration of $5 \times 10^6$ cells/ml in 199 medium (Gibco Ltd) supplemented with 1% BSA (Cohn Fr. V. Sigma, St. Louis), L-glutamine 2 mM and 10 mcg/ml of gentamycin sulfate (Schering, Klworth, N.J., U.S.A.) (TC 199-BSA). The cells have been used when their viability was over 95% at the Trypan Blue exclusion test.

Thy 1.2 Antigen Induction Bioassay

Two hundred μl of the spleen MNC suspension have been mixed with the same volume of the tripeptide opportunely diluted with TC 199-BSA medium. The control cells have only been treated with the medium TC 199-BSA. All the cells have been incubated for 18 hours at 37° C. in humidified atmosphere containing 5% CO2, then washed twice with HBSS containing 5% heat-inactivated neonatal calf serum (Gibco) (HBSSS-CS) and finally resuspended in the same medium at a concentration of 10⁶ cells/ml.

Direct Immunofluorescence (IF)

The expression of Thy 1.2 antigen was analyzed by IF using and anti-Thy 1.2 monoclonal antibody conjugated with fluorescein (Bio-Yeda, supplied by Technogenetics, S. Mauro Torinese, Italy) at the concentration of 2 mcg/10⁶ cells. The cells have been incubated with the antibody for 30 minutes at 4° C.

After three washes in HBSS, the cells have been resuspended in the same medium and observed with a Leitz Orthomat microscope equipped with epiillumination.

At least 300 cells have been counted in each evaluation.

Results

As shown in the table, the tripeptide Arg-Gly-Asp is active in vitro in the induction of Thy 1.2 induction at concentrations ranging from 1 and 200 µg/ml, the optimum concentration being 10 mcg/ml.

| ARG—GLY—ASP CONCENTRATION (µg/ml) | HOURS OF INCUBATION | % THY 1.2 + CELLS | VARIATION |
|---|---|---|---|
| — | 3 | 22.0 | — |
| 0.1 | 3 | 25.3 | +3.3 |
| 1 | 3 | 27.1 | +5.1 |
| 10 | 3 | 31.4 | +9.4 |
| 100 | 3 | 29.4 | +7.4 |
| 200 | 3 | 27.9 | +5.9 |
| — | 18 | 17.0 | — |
| 10 | 18 | 26.5 | +9.5 |
| 100 | 18 | 21.7 | +4.7 |

RNA synthesis in PHA-stimulated human T lymphocytes in vitro

Human T lymphocytes, incubated in vitro for 24 hours in presence of 0.5% phytohemagglutinin (PHA) and different concentrations of the tripeptides under examination, have been analyzed for RNA synthesis (cell activation) by means of 3H-uridine labelling.

The results, shown in the table, evidence that both Arg-Gly-Asp and Arg-Gly-D-Asp are able to increase PHA-induced human T lymphocyte activation.

| PEPTIDE CONCENTRATION | ARG—GLY—ASP c.p.m. | | ARG—GLY—D—ASP c.p.m. | |
|---|---|---|---|---|
| mcg/ml | X̄ ± S.E. | Δ % | X̄ ± S.E. | Δ % |
| 0 | 3835 108 | — | 3835 108 | — |
| 0.0001 | 3703 198 | −3 | 3517 242 | −8 |
| 0.001 | 3741 168 | −2 | 4129 91 | +8 |
| 0.01 | 4259 191 | +11 | 4283 114 | +12 |
| 0.1 | 4516 127 | +18 | 4777 180 | +25 |
| 1 | 4068 278 | +6 | 4682 456 | +22 |
| 10 | 4199 241 | +9 | 4346 403 | +13 |

DNA synthesis in PHA-stimulated human T lymphocytes in vitro

Human T lymphocytes, incubated in vitro for 72 hours in presence of 0.5% PHA and different concentrations of the tripeptides under examination, have been analyzed for DNA synthesis (cell proliferation) by means of 3H-thymidine labelling.

The results, shown in the table, evidence that both Arg-Gly-Asp and Arg-Gly-D-Asp are able to increase PHA-induced human T lymphocyte proliferation.

| PEPTIDE CONCENTRATION | ARG—GLY—ASP c.p.m. | | ARG—GLY—D—ASP c.p.m. | |
|---|---|---|---|---|
| mcg/ml | X̄ ± S.E. | Δ % | X̄ ± S.E. | Δ % |
| 0 | 22642 3688 | — | 22642 3688 | — |
| 0.0001 | 22002 3383 | −3 | 21898 3912 | −3 |
| 0.001 | 23519 3712 | +4 | 23029 3235 | +2 |
| 0.01 | 24034 3625 | +6 | 24551 3322 | +8 |
| 0.1 | 25814 3931 | +17 | 26090 3435 | +15 |
| 1 | 25163 3805 | +11 | 26170 4600 | +16 |
| 10 | 24111 3537 | +6 | 24570 4201 | +9 |

Effect on cell cycle

Human T lymphocytes have been incubated for 72 hours in presence of PHA and the tripeptides under examination (1 µg/ml). DNA has then been stained with propidium iodide and cells have been analyzed with a flow cytometer.

| | CELL PHASES | | | | | |
|---|---|---|---|---|---|---|
| | Go-G1 | | S | | G2 + M | |
| | % CELLS | | % CELLS | | % CELLS | |
| T + PHA | 63.36 | — | 30.61 | — | 6.02 | — |
| T + PHA + ARG—GLY—ASP | 57.69 | −5.67 | 29.46 | −1.15 | 12.14 | +6.12 |
| T + PHA + ARG—LYS—ASP | 60.79 | −2.57 | 30.63 | +0.02 | 9.42 | +3.40 |
| T + PHA + | | | | | | |

-continued

| | CELL PHASES | | | | | |
|---|---|---|---|---|---|---|
| | Go-G1 | | S | | G2 + M | |
| | % CELLS | | % CELLS | | % CELLS | |
| ARG—LYS—GLU | 56.15 | −7.21 | 28.64 | −1.97 | 14.35 | +8.33 |

Go = resting cells
G1 = interval between mitosis and DNA synthesis
S = DNA synthesis
G2 = interval between DNA synthesis and mitosis
M = mitosis Stimulation of lymphokine production in vitro Human T lymphocytes have been incubated with PHA and with or without the peptides under examination for 24 hours (in the case of IL-2) or 72 hours (in the case of BCGF).

The supernatants have been collected, filtered (0.2 μm) and assayed for the presence of IL-2 or BCGF activity, by adding them at different concentrations to fresh T lymphocytes or to long term cultured B cells. The proliferating activity of these cells, dependent on the presence of the respective growth factor, has been evaluated through 3H-thymidine incorporation.

The results evidence a marked effect of stimulation of the growth factor production by Arg-Gly-Asp, slightly lower than that of Arg-Lys-Glu, but higher than that obtained with Arg-Lys-Asp.

Stimulation of the lymphokine in vitro by pure human T lymphocytes, without macrophages The lymphokine production by human T lymphocytes purified through massage on nylon wool column has been evaluated with the same methods as in the previous experiment.

T cell purity was above 95%, while macrophages/monocytes as well as B cells were under 1%. In order to obviate the lack of macrophages, recombinant IL-1 β (Genzyme) has been added at the concentration of 25 Units/ml.

The results obtained, both for IL-2 and BCGF, show that the effect of Arg-Gly-Asp is comparable with that of the other reference compounds, among which also thymosin fraction 5, a partially purified thymic derivative, has been used.

| SUPERNATANT FROM: | N° of data | 3.125 | | 6.25 | | 12.5 | | 25 | | 50 | |
|---|---|---|---|---|---|---|---|---|---|---|---|
| | | $\bar{X} \pm$ S.E. | Δ % | $\bar{X} \pm$ S.E. | Δ % | $\bar{X} \pm$ S.E. | Δ % | $\bar{X} \pm$ S.E. | Δ % | $\bar{X} \pm$ S.E. | Δ % |
| BCGF ACTIVITY (COUNTS PER MINUTE) AT THE PERCENTAGE OF SUPERNATANT: | | | | | | | | | | | |
| T + PHA | 2 | 1345 627 | — | 2156 193 | — | 5402 290 | — | 15030 2294 | — | 17297 1650 | — |
| T + PHA + ARG—LYS—GLU | 2 | 5377 2459 | +300 | 10125 4503 | +370 | 18143 3006 | +236 | 21977 2702 | +46 | 22666 3930 | +31 |
| T + PHA + ARG—GLY—ASP | 2 | 4800 2377 | +257 | 8611 3875 | +299 | 16550 2312 | +206 | 18645 2489 | +24 | 20508 368 | +19 |
| T + PHA + ARG—LYS—ASP | 2 | 3624 1706 | +169 | 6455 2328 | +199 | 12219 1346 | +126 | 16554 4076 | +10 | 16107 1629 | −7 |
| TCGF ACTIVITY | | | | | | | | | | | |
| T + PHA | 2 | 1564 329 | — | 2622 643 | — | 4012 1136 | — | 7824 2657 | — | 14086 3241 | — |
| T + PHA + ARG—LYS—GLU | 2 | 4516 1320 | +189 | 10213 4526 | +290 | 16609 6126 | +314 | 20695 5001 | +165 | 18451 2176 | +31 |
| T + PHA + ARG—GLY—ASP | 2 | 3245 470 | +107 | 8496 4359 | +224 | 13113 4249 | +227 | 16609 6126 | +105 | 18167 3231 | +29 |
| T + PHA + ARG—LYS—ASP | 2 | 3478 1340 | +122 | 8139 4253 | +210 | 13977 6492 | +248 | 15911 5237 | +103 | 16476 5889 | +17 |

| Supernatant from: | 3.125 | | 6.25 | | 12.5 | | 25 | | 50 | |
|---|---|---|---|---|---|---|---|---|---|---|
| | c.p.m. | Δ % | c.p.m. | Δ % | c.p.m. | Δ % | c.p.m. | Δ % | c.p.m. | Δ % |
| BCGF ACTIVITY AT THE PERCENTAGE OF SUPERNATANT | | | | | | | | | | |
| T + PHA + IL − 1 | 318 | — | 582 | — | 1104 | — | 2507 | — | 5056 | — |
| T + PHA + IL − A + ARG—LYS—GLU (1 mcg/ml) | 349 | +10 | 564 | −3 | 2866 | +160 | 4622 | +84 | 10099 | +100 |
| T + PHA + IL − 1 + ARG—LYS—GLU (10 mcg/ml) | 622 | +96 | 784 | +35 | 3196 | +189 | 7187 | +187 | 13863 | +174 |
| T + PHA + IL − 1 + ARG—ALA—ARG (1 mcg/ml) | 496 | +56 | 516 | −11 | 2347 | +113 | 3987 | +59 | 7143 | +41 |
| T + PHA + IL − 1 + ARG—ALA—ARG (10 mcg/ml) | 312 | −2 | 425 | −27 | 2569 | +133 | 4437 | +77 | 9185 | +82 |
| T + PHA + IL − 1 + ARG—GLY—ASP (1 mcg/ml) | 618 | +94 | 634 | +9 | 2663 | +141 | 5172 | +106 | 9837 | +95 |
| T + PHA + IL − 1 + ARG—GLA—ASP (10 mcg/ml) | 784 | +147 | 866 | +49 | 2997 | +171 | 6849 | +173 | 11364 | +125 |
| T + PHA + IL − 1 + ARG—GYS—ASP (1 mcg/ml) | 326 | +3 | 370 | −36 | 1839 | +67 | 3186 | +27 | 8942 | +77 |
| T + PHA + IL − 1 + ARG—LYS—ASP (10 mcg/ml) | 421 | +32 | 462 | −21 | 1847 | +67 | 2946 | +18 | 6802 | +35 |
| T + PHA + IL − 1 + THYMOS.F5 | 418 | +31 | 921 | +58 | 1796 | +63 | 3127 | +25 | 11529 | +128 |

-continued

| Supernatant from: | 3.125 | | 6.25 | | 12.5 | | 25 | | 50 | |
|---|---|---|---|---|---|---|---|---|---|---|
| | c.p.m. | Δ % | c.p.m. | Δ % | c.p.m. | Δ % | c.p.m. | Δ % | c.p.m. | Δ % |
| (100 mcg/ml) | | | | | | | | | | |
| T + PHA + IL − 1 + THYMOS.F5 (200 mcg/ml) | 716 | +125 | 566 | −3 | 1308 | +18 | 2132 | −15 | 6721 | +33 |
| TCGF ACTIVITY | | | | | | | | | | |
| T + PHA +IL − 1 | 1696 | — | 2817 | — | 3663 | — | 4812 | — | 6297 | — |
| T + PHA + IL − A + ARG—LYS—GLU (1 mcg/ml) | 2516 | +48 | 8218 | +192 | 14932 | +308 | 17148 | +256 | 16293 | +159 |
| T + PHA + IL − 1 + ARG—LYS—GLU (10 mcg/ml) | 2873 | +69 | 7192 | +155 | 15264 | +317 | 16887 | +251 | 12246 | +94 |
| T + PHA + IL − 1 + ARG—ALA—ARG (1 mcg/ml) | 2085 | +23 | 5679 | +102 | 11728 | +220 | 12692 | +164 | 11378 | +81 |
| T + PHA + IL − 1 + ARG—ALA—ARG (10 mcg/ml) | 3142 | +85 | 6447 | +129 | 13629 | +272 | 15143 | +215 | 10875 | +73 |
| T + PHA + IL − 1 + ARG—GLY—ASP (1 mcg/ml) | 1984 | +17 | 6893 | +145 | 13147 | +259 | 14862 | +209 | 15654 | +149 |
| T + PHA + IL − 1 + ARG—GLY—ASP (10 mcg/ml) | 1736 | +2 | 6342 | +125 | 13874 | +279 | 10968 | −128 | 13427 | −113 |
| T + PHA + IL − 1 + ARG—LYS—ASP (1 mcg/ml) | 2274 | +34 | 5216 | +85 | 8969 | +145 | 10421 | +117 | 9887 | +57 |
| T + PHA + IL − 1 + ARG—LYS—ASP (10 mcg/ml) | 2769 | +63 | 6143 | +118 | 7245 | +98 | 7963 | −65 | 8143 | −29 |
| T + PHA + IL + THYMOS.F5 (100 mcg/ml) | 2374 | +40 | 7286 | +159 | 15637 | +327 | 13142 | +173 | 13835 | +120 |
| T + PHA + IL + THYMOS.F5 (200 mcg/ml) | 2156 | +27 | 5218 | +85 | 12143 | +232 | 10874 | +126 | 12139 | +93 |

EXAMPLE 4

Toxicological Trials

Arg-Gly-Asp

The tripeptide Arg-Gly-Asp shows a LD50 higher than 1000 mg/kg i.p. in mice.

EXAMPLE 5

Clinical Use

The previous examples 3 and 4 have shown that the tripeptides which are the object of the present invention are active in vitro as immunostimulating agents in both animal and human experimental models, and in vivo as antimetastatic products in laboratory animals, beyond being devoid of toxicity.

Thus, it can be predicted very reasonably that they will be clinically userful in preventing metastatization in patients who undergo surgical tumour removal, at the same time improving the immune defenses of the organism thanks to their immunostimulating properties.

Salts of the Tripeptides

The above mentioned examples are referred to the acetate salt of the tripeptides. However, it is possible to obtain analogous results with other salts of organic and inorganic acids, such as for instance trifluoroacetate, hydrochloride, sulfate.

We claim:

1. A method of treating a metastatic disorder comprising administering to a subject in need of treatment, a pharmaceutically effective amount of a tripeptide of the general formula X-Gly-Y where X is L-Arg or D-Arg and Y is L-Asp or D-Asp, or a pharmaceutically acceptable salt thereof.

2. A method of treating an immunological disorder comprising administering to a subject in need of treatment, a pharmaceutically effective amount of a tripeptide of the general.formula X-Gly-Y where X is L-Arg or D-Arg and Y is L-Asp or D-Asp, or a pharmaceutically acceptable salt thereof.

3. A method according to claim 2 which comprises orally administering the tripeptides or a pharmaceutically acceptable salt thereof.

4. A method according to claim 2 which comprises parenterally administering the tripeptides or a pharmaceutically acceptable salt thereof.

5. A method according to claim 1 which comprises parenterally administering the tripeptides or a pharmaceutically acceptable salt thereof.

6. A method according to claim 1 which comprises administering the tripeptides or a pharmaceutically acceptable salt thereof.

7. A method for reducing metastases and improving the immune response of a subject who has undergone surgical removal of a tumor, comprising administering a pharmaceutically effective amount of a tripeptide the general formula X-Gly-Y wherein X is L-Arg or D-Arg and Y is L-Asp or D-Asp, or a pharmaceutically acceptable salt thereof.

8. A method according to claim 1 including administering acetate salts of the tripeptides.

9. A method according to claim 6 including administering trifluoroacetate salts of the tripeptides.

10. A method according to claim 6 including administering hydrochloride salts of the tripeptides.

11. A method according to claim 6 including administering sulfate salts of the tripeptides.

* * * * *